United States Patent [19]

Maddess

[11] Patent Number: 5,295,495
[45] Date of Patent: Mar. 22, 1994

[54] GLAUCOMA TESTING FROM OBSERVATIONS OF OPTOKINETIC NYSTAGMUS

[75] Inventor: Teddy L. Maddess, Kaleen, Australia

[73] Assignee: The Australian National University, Australia

[21] Appl. No.: 882,111

[22] Filed: May 13, 1992

[30] Foreign Application Priority Data

May 13, 1991 [AU] Australia ............... PK 6087

[51] Int. Cl.$^5$ ................................. A61F 9/00
[52] U.S. Cl. .................. 128/898; 128/745; 128/645; 351/246
[58] Field of Search .............. 128/898, 745, 645; 351/209–211, 221, 222, 237, 239, 246

[56] References Cited

U.S. PATENT DOCUMENTS

| | | | |
|---|---|---|---|
| 1,827,954 | 10/1931 | Ohm | 351/211 |
| 3,469,903 | 9/1969 | Grichnik | 351/209 |
| 4,155,352 | 5/1979 | Toglia et al. | 128/745 |
| 4,634,243 | 1/1987 | Massof et al. | 351/243 |
| 4,676,611 | 6/1987 | Nelson et al. | 128/745 |
| 4,832,480 | 5/1989 | Kornacker et al. | 128/731 |

FOREIGN PATENT DOCUMENTS 2029851 12/1971 Fed. Rep. of Germany ...... 351/210

*Primary Examiner*—Stephen C. Pellegrino
*Assistant Examiner*—Jeffrey A. Schmidt
*Attorney, Agent, or Firm*—Sughrue, Mion, Zinn Macpeak & Seas

[57] ABSTRACT

Optokinetic nystagmus is the rhythmical scanning of the eyes when primates attempt to stabilize constantly moving visual scenes. If a pattern having distinct vertical features is projected onto a screen and is drifted to the left or to the right, variations of certain parameters associated with optokinetic nystagmus of a subject observing the drifting pattern from the values of those parameters for persons having normal, healthy vision provide an indication of damage to M-type ganglion cells due to the presence of glaucoma in the subject. Such variations occur at an early stage of glaucoma, before other positive indications of the disease are present. Preferably the projected pattern is a coarse sinusoidal grating with vertical striations, which is temporally modulated by a rapid movement or flicker.

13 Claims, No Drawings

GLAUCOMA TESTING FROM OBSERVATIONS OF OPTOKINETIC NYSTAGMUS

TECHNICAL FIELD

This invention concerns the detection of the eye disease glaucoma. More particularly, it concerns the detection of neural damage which is indicative of the presence of the eye disease glaucoma, using observations of optokinetic nystagmus (the rhythmical scanning of the eyes which occurs when primates attempt to stabilize constantly moving visual scenes). Using the method of the present invention, a person suffering from glaucoma can be diagnosed as such before the disease reaches the stage where prospects for successful treatment are poor and irreversible blindness is almost inevitable.

BACKGROUND TO THE INVENTION

In the eye, the final stage of image processing in the retina is performed by retinal ganglion cells. The axons of the retinal ganglion cells project out of the eye to the optic nerve. Glaucoma, which produces irreversible blindness if not treated early enough, destroys these ganglion cells. A classical diagnostic feature of glaucoma is the occurrence of a scotoma (the disappearance of a portion of the peripheral visual field). Unfortunately, by the time a scotoma is detected, the disease has reached a stage where treatment is able to do little more than possibly prevent the occurrence of further blindness. Another classical epidemiological feature of glaucoma is the "cupping" of the optic disc, or papilla, which to some extent reflects the loss of ganglion cell axons.

One approach that has been used to assist in the diagnosis of glaucoma before scotomas have developed is to test the intraocular tension of patients. Tests of intraocular tension, however, often involve the use of drugs, are time consuming, and can be unpleasant for the patient. In some cases, potentially damaging elevated tensions occur only transiently and at unpredictable times during the day. Such transient high tensions may not be detected. Moreover, up to half of all glaucoma patients do not exhibit sustained ocular tensions above 21 mm of mercury (these patients are described as having "low-tension" or "normal-tension" glaucoma). Thus, testing the intraocular tension of a person is not a reliable method for the early detection of glaucoma.

Other proposals for the early detection of glaucomatous retinal damage have involved the assessment of color vision defects. Simple tests of color vision defects, however, have shown a lack of correlation between the defects noted and the presence of optic disk cupping. More complex tests of color vision defects, involving anomaloscopy, are too difficult for clinical use. Moreover, those tests cannot differentiate between color vision defects caused by glaucoma and color deficits caused by other neurological disorders, such as amblyopia and optic neuritis. In addition, it has been reported that up to 25 per cent of patients who have glaucomatous scotoma show no color defects. Thus, assessment of color vision deficits is not a reliable method of detecting glaucoma in its early stages, even if it should become practical to perform detailed color vision tests clinically.

Another problem with psychophysical measurements of visual performance is that the results of such measurements vary significantly among subjects with normal vision. This natural variance reduces the ability to use such measurements to distinguish normal subjects from those with early glaucomatous damage. There has been a long-felt need, therefore, for a method of measuring visual performance which is less subjective than the psychophysical tests that have been carried out hitherto.

DISCLOSURE OF THE PRESENT INVENTION

The prime objective of the present invention is the provision of a relatively non-invasive, easy to perform, reliable test for glaucomatous retinal damage, which enables the presence of glaucoma to be detected at an early stage and which is fundamentally a less subjective measure of visual performance than the results of the currently used psychophysical tests tend to be.

To achieve this objective, the present invention utilizes measurements of the performance of the optokinetic nystagmus system, when it is stimulated by a particular class of visual stimuli (patterns), to differentiate normal subjects from persons with glaucomatous damage. The patterns are believed to specifically stimulate a group of retinal ganglion cells, the number of which is indicative of the level of glaucomatous damage.

Ganglion cells of higher primates are known to be of two types, namely "M" type ganglion cells and "P" type ganglion cells, each of which respond to visual stimuli. However, the P type ganglion cells respond in a sluggish manner and their physiologically recorded responses indicate that they do not contribute to the sensing of certain types of images, including the images with which the present invention is concerned. The M-type cells consist mainly of two physiological classes, namely, the physiological "y-type" cells (usually designated "$M_y$-cells") and the physiological "x-type" cells (usually designated "$M_x$-cells"). Each type of cell is distributed across the retina in a distribution which is most dense at the fovea, or central visual area, and more diffuse toward the peripheral regions of the retina which correspond to the peripheral visual field. There are significantly fewer $M_y$-cells than $M_x$-cells.

In 1966, D H Kelly reported, in his paper entitled "Frequency doubling in visual responses" (which was published in the *Journal of the Optical Society of America*, Volume 56, page 1628), that when sinusoidal gratings with spatial frequencies below 1 cycle per degree are modulated so that the contrast between the bars or striations of the pattern is varied at rates higher than 10 Hz, the gratings appear as frequency-doubled sinusoids to persons of normal vision. D H Kelly's subsequent work (reported in his paper entitled "Nonlinear visual responses to flickering sinusoidal gratings", which was published in the *Journal of the Optical Society of America*, Volume 71, page 1051, 1981), has shown that this second-harmonic distortion of the human visual response is due to the neural pathway between the eye and the brain having both a linear and a non-linear component.

More recent work indicates that the $M_y$-cells are responsible for the non-linear component of the visual illusion described as the frequency doubled illusion of D H Kelly. Recent work has also indicated that patients having glaucoma also suffer a diffuse, and not just a localized, loss of ganglion cells. Other recent work indicates that when, as in the experiments of D H Kelly, the sinusoidal patterns are displayed over a region of the visual field which subtends solid angles of more than a few tenths of a steradian about the central visual axis, the best spatial frequency for eliciting the frequency doubled illusion is largely determined by the peripheral portions of the displayed stimulus. There are also data available to show that the M-cells as a whole are more affected in early glaucoma (see, for example, the paper by H A Quigley et al. entitled "Chronic glaucoma damages large optic nerve fibers", which was published in *Investigative Ophthalmology and Visual Science*, Volume 28, page 913, 1987).

It also appears that optokinetic nystagmus (OKN) may be subserved at least in part by M-cells which terminate in the dorsal Lateral Geniculate Nucleus (dLGN). Optokinetic nystagmus, the rhythmical scanning of the eyes that is produced when animals attempt to stabilize constantly moving visual scenes, appears to consist of two components: (a) the so-called direct fast pathway, and (b) the indirect slow pathway containing the so-called velocity storage mechanism (see the paper by T Raphan, V Matsuo and B Cohen, entitled "Velocity storage in the vestibulo-ocular reflex arc (VOR)", which was published in *Experimental Brain Research*, Volume 35, page 229, 1979). During OKN the eyes drift slowly to keep pace with moving visual scenes and periodically execute a flick back in the reverse direction to maintain the average position of the eye looking forward. In humans, ocular following is dominated by information in the direct pathway, which takes its input from the visual cortex.

Experimental investigations, using monkeys, of the independent effect on optokinetic nystagmus of lesions and stimulation of the nucleus of the optic tract (NOT) and of the adjacent Dorsal Terminal Nucleus (DTN), and also electrophysical recording from the NOT-DTN, have indicated that the information about the indirect slow system in higher primates travels to the oculomotor system and back to the vestibular system via the neurons of the NOT-DTN. The experiments involving lesions have been reported in the paper by D Schiff, B Cohen, J Buttner-Ennever and V Matsuo, entitled "Effects of lesions of the nucleus of the optic tract on optokinetic nystagmus and after-nystagmus in the monkey", which was published in *Experimental Brain Research* Volume 79, page 225, 1990. The work on stimulation was reported in the paper by D Schiff, B Cohen and T Raphan, entitled "Nystagmus induced by stimulation of the nucleus of the optic tract in the monkey", which was published in *Experimental Brain Research*, Volume 70, page 1, 1988. The experiments with electrophysiological recording from the NOT-DTN have been detailed in the paper by K P Hoffmann and C Distler, entitled "Quantitative analysis of visual receptive fields of neurons in the nucleus of the optic tract and dorsal terminal nucleus of the accessory optic tract in macaque monkey", published in *Journal of Neurophysiology*, Volume 62, page 416, 1989.

In higher mammals, neurons of the NOT receive visual input from the retina and from the visual cortex. This linkage is best established in cats, where it appears that the input proceeds via the supersylvian visual areas (see the paper by R J Tusa, J L Demer and S J Herdman, entitled "Cortical areas involved in OKN and VOR in cats: cortical lesions", which was published in *The Journal of Neuroscience*, Volume 9, page 1163, 1989). The supersylvian areas, in turn, receive much of their input from area 18 and area 17. Area 17 principally receives input from the y-cells of the Lateral Geniculate Nucleus (LGN), and the part of area 17 projecting to the supersylvian is also dominated by y-cell input from the LGN. Analogs of the supersylvian regions of the cat's brain exist in primates and these appear to feed the NOT-DTN with information arising from M-cells. The cortical input to the NOT-DTN system, and also to the Optokinetic Nystagmus (OKN) reflex, is thus dominated by input from the fast conducting M-cell pathway. In primates, unlike the situation in cats, all the NOT-DTN cells appear to be binocular, which is a sign of cortical input. Also unlike cats, only about 30 per cent of primate NOT-DTN cells appear to receive input directly from the eye (see the paper by K P Hoffman, C Distler, R G Erickson and W Mader, entitled "Physiological and anatomical identification of the nucleus of the optic tract and dorsal terminal nucleus of the accessory optic tract in monkeys", published in *Experimental Brain Research*, p 635, 1988).

Thus, it would be expected that the OKN behavior of primates is influenced by pathology of the M-cell visual pathway as seen in glaucoma. However, the vestibular ocular system is renowned for its ability to adapt its gain and timing to counteract pathology, so the expected effects of early pathology might be subtle. In particular, a reduction in visual input as a result of retinal cell death might be compensated by an increase in gain at the NOT-DTN. Such an increase in gain, however, cannot increase the signal to noise ratio at the level of the NOT-DTN, so evidence of a deterioration of signal to noise ratios at the NOT-DTN level of input to the optokinetic system might be expected if glaucoma is present. The velocity storage mechanism, and also the slow phase of optokinetic nystagmus, has been shown many times to be rapidly reset by sensory input which is inconsistent with continuous scene motion. In a situation in which the signal to noise ratio of the visual input provided to the OKN system decreases, one might expect the slow phase velocity to show long term variations indicative of the OKN system partially resetting its estimate of the slow phase velocity in response to unreliable visual input.

The present inventor has hypothesized that, if this latest work is correct, the following conclusions may be reached:

(a) To use visual stimuli to assess glaucomatous damage (as distinct from damage caused by other disorders such as amblyopia, optic neuritis or Parkinson's disease), it would be necessary to use visual stimuli which preferentially stimulate the M retinal ganglion cell pathway. Stimuli producing the frequency doubled illusion seem to provide this assurance because the illusion would appear to be due to the response of the $M_y$-cells alone. Similar stimuli, which would tend to favor stimulation of the M-cell pathway as a whole, particularly stimuli dominated by high temporal frequencies and low spatial frequencies, and which drift so as to drive the OKN system, would also provide evidence of glaucomatous damage.

(b) Impairment of a person's ability to see the frequency doubled illusion and closely related stimuli should be relatively specific to glaucoma. This is because the visual deficits produced by other common neurological disorders (such as optic neuritis, amblyopia, and Parkinson's disease) occur within a different spatio-temporal pass band. Persons who have these other common disorders show visual impairment with respect to their ability to see high spatial frequencies presented at low temporal frequencies (which is the opposite of the requisite conditions for seeing the frequency doubled illusion, namely, low spatial frequencies presented at high temporal frequencies).

(c) Since the vestibular ocular system is known for its ability to adapt, one would not expect the chronic and progressive loss of ganglion cells to cause the optokinetic gain to be reduced. Instead, one would expect that the signal to noise ratio of the processes controlling optokinetic nystagmus would be upset, leading to more variable, rambling OKN velocities, beat durations and beat sizes as the "indirect" system acts on noisy visual input. Since the OKN system's velocity storage mechanism might be driven into a state of continuous resetting, parameters such as OKN beat duration or rate should also be affected.

(d) One would thus expect that visual stimuli producing the frequency doubled illusion, and also stimuli sharing many of the spatio-temporal qualities of those producing the frequency doubled illusion, would allow glaucomatous damage to be assessed by measurement of various parameters related to the variability of optokinetic nystagmus, which would be observed when these patterns are caused to drift across the visual field.

(e) Specific parameters such as the variance and total variation of the OKN slow phase velocity or beat size or duration would thus be expected to be good indicators of glaucomatous damage.

Accordingly, the present inventor predicted, and has now demonstrated that this is the case, it should be possible to diagnose the presence of glaucoma at an early stage of the disease by a method which involves measuring a set of parameters which quantify aspects of optokinetic nystagmus which are believed to indicate glaucomatous damage. The measured parameters selected by the present inventor are thought to be directly related to the ability of the optokinetic system to assess and maintain its estimate of actual stimulus velocity in the presence of glaucomatous damage. Preferably, the selected parameters are used in combinations to form a discriminant function which is used to predict whether a person's OKN performance is normal or is indicative of glaucomatous damage.

According to the present invention, a method for diagnosing the occurrence of glaucoma in a subject comprises the steps of:

(1) presenting to the subject a regular pattern having distinct vertical features, the distinct vertical features comprising a relatively low spatial frequency (or a collection of relatively low spatial frequencies), and having a contrast which is modulated at a relatively high temporal frequency, said modulation being effected by a translation of the pattern image across the subject's retina and/or by direct contrast modulation of the pattern features, at a frequency which is sufficient, or nearly sufficient, for a frequency doubled illusion to be perceived by persons of normal vision who observe the pattern; and moving the pattern laterally, at a constant rate, to either the left or the right;

(2) monitoring the optokinetic nystagmus of the subject during the movement of the pattern and determining at least one of the parameters in the group consisting of (a) standard deviation of optokinetic nystagmus slow phase velocity;

(b) standard deviation of the optokinetic beat duration;

(c) the mean optokinetic nystagmus beat duration for those optokinetic nystagmus beats having a slow phase which is well represented in a graphical display by a straight line;

(d) the standard deviation of the optokinetic nystagmus beat duration for those optokinetic nystagmus beats having a slow phase which is well represented in a graphical display by a straight line;

(e) the 95 per cent confidence limit in the mean duration of the optokinetic nystagmus beats for those beats which have a slow phase eye position with time which is well represented in a graphical display by a straight line;

(f) the standard deviation of the optokinetic nystagmus beats which occur within contiguous clusters of beats;

(g) the mean rate of optokinetic nystagmus beats which occur within contiguous clusters of beats;

(h) the mean eye deflection (in degrees) per optokinetic nystagmus beat of optokinetic nystagmus beats which occur within contiguous clusters of beats; and (i) the relative total variation in optokinetic nystagmus beat velocity for those optokinetic nystagmus beats which have a slow phase that is well represented (in a graphical display) by a straight line; and (3) comparing the (or each) determined parameter, or a linear combination of these parameters forming a discriminant function, with the value of that parameter expected for a person with normal, healthy vision.

Preferably more than one of the parameters (a) to (i) are determined, and more preferably at least the parameters (a), (b), (e), (g) and (h) are determined.

Normally, the pattern presented to the subject will be a sinusoidal grating pattern, with substantially vertical striations.

The lateral movement of the periodic pattern is preferably at a rate within the range of from 4 pattern cycles per second (4 Hz) to 10 pattern cycles per second (10 Hz).

Repeat determinations of several (preferably all) of the chosen parameters of the group consisting of the above-listed parameters (a) to (i) will be obtained for a subject, to provide maximum confidence in the result of the diagnosis.

To illustrate the present invention, and to demonstrate the relationship between the parameters listed above and the presence of glaucomatous damage in a subject, one set of experiments, out of a series of sets of experiments, will now be described (by way of example only).

DETAILED DESCRIPTION OF EXEMPLARY SET OF EXPERIMENTS

The experiments involved measuring a subject's eye position as a function of time while the subject viewed drifting visual patterns. Measurements were made on each subject for each of four different stimuli. The four stimuli consisted of patterns of sinusoidal intensity gratings having vertical "bars", which were moved or drifted either to the left or to the right, with and without temporal modulation of contrast. The patterns were all described by the equation:

$$I(x,t) = I_O + C(t)I_O \sin[2\pi(fx - \Omega t)] \qquad (1)$$

where $I_O$ is the background intensity, C(t) is a function describing the temporal modulation of the contrast, f is the spatial frequency with units of cycles per degree (c.p.d.), $\omega$ is the temporal frequency generated by the drift of the pattern with units of Hz, and x and t correspond to space and time measured in degrees and seconds respectively.

In the experiments conducted by the present inventor, the visual stimuli were presented on the face of a rectangular video monitor so that the stimuli subtended 31.4° in the horizontal direction and 27.7° in the vertical direction. The mean luminance, $I_o$, was 52 candela per square meter. In terms of equation (1), the spatial frequency (f) in all cases was 0.25 c.p.d. and the temporal frequency due to pattern drift ($\omega$) was ±6.79 Hz. The function C(t) in equation (1) was a square wave modulated by 1 or −1, or some amount less than 1, at a predetermined rate. In this set of experiments, two modulation rates of C(t) were used: 27.2 Hz or 0 Hz. In other words, measurements were obtained for each of the following four stimulus paradigms:

1) C(t) modulated at 27.2 Hz, drift direction left to right;
2) C(t) modulated at 27.2 Hz, drift direction right to left;
3) C(t) modulated at 0 Hz, drift direction left to right; and
4) C(t) modulated at 0 Hz, drift direction right to left.

In all four cases, the spatial frequency and drift frequency were 0.25 c.p.d. and 6.79 Hz respectively. The first two stimuli, with contrast modulation at 27.2 Hz, produced the frequency doubled illusion while the second two stimuli, with no modulation of contrast, provided near frequency doubled stimulation of the OKN system. In experiments using the first and second stimulus paradigms, the magnitude of C(t) alternated between +0.6 and −0.6. In the experiments using the third and fourth stimulus paradigms, the magnitude of C(t) was 0.4.

The subjects used in the experiments consisted of two groups of roughly age matched persons. The first group were persons of normal (healthy) vision. The second group consisted of glaucoma suspects or glaucoma sufferers. This second group will hereinafter be referred to as the "test" group and the first group will be termed the "normal" group. Positive diagnosis of glaucoma depended upon the presence of glaucomatous scotoma. Glaucoma suspects were classified by the lack of glaucomatous scotoma, but the presence of suspect pathological optic disk appearance and a history of elevated tension in one or both eyes.

During each experiment, the eye position of a subject was measured by standard electroculogram techniques. However, other known methods of measuring eye position could have been used. The data obtained was low pass filtered with a 40 db per octave roll off above 200 Hz. Data was then digitized to 12-bit accuracy and recorded on line to the hard disc of a computer. Analysis of the eye position data was conducted off line and consisted of identification of individual OKN beats and their relative position in the eye movement record. Data was digitally filtered with a zero phase shift, 50 Hz notch filter to remove noise. A total of 78 parameters were measured. These parameters were subjected to discriminant analysis, also known as canonical variate analysis, to see if some parameter or combination of parameters could produce a linear discriminant function which could reliably discriminate the normal from the glaucoma test group.

The OKN parameters which proved to be of value in forming a discriminant function are as follows:

TV—The total variation in OKN beat velocity.

TVwf—The total variation in OKN beat velocity for those OKN beats whose slow phase was well described (fit) by a straight line.

RTVwf—The relative total variation in OKN beat velocity for those OKN beats having a slow phase which is well described by a straight line in a graphical presentation.

SDV—The standard deviation in the OKN slow phase velocity.

SDOKT—The standard deviation in the OKN beat duration.

SDwfOKT—The standard deviation in the OKN beat duration for those OKN beats which have a slow phase which is well described by a straight line in a graphical presentation.

SDGapT—The standard deviation in the duration of gaps between clusters of OKN beats.

MedGapT—The median duration of gaps between clusters of OKN beats.

MwfOKT—The mean OKN beat duration for those OKN beats which have a slow phase which is well described by a straight line in a graphical presentation.

MOKR—Mean rate of OKN beats generated.

MclOKR—Mean rate of OKN beats occurring within contiguous clusters of beats.

MclOKT—Mean duration of OKN beats occurring within contiguous clusters of beats.

MclOKS—Mean eye deflection degrees per OKN beat of OKN beats occurring within contiguous clusters of beats.

CLwfOKT—The 95 per cent confidence limit in the mean OKN beat duration for those OKN beats where slow phase eye position with time is well described by a straight line in a graphical presentation.

Much of the nomenclature in this list is standard in this field but some terms found in the above list of parameters, namely: slow phase velocity, gaps, OKN beats, clusters of OKN beats, total variation, and relative total variation, may require explanation to some workers of limited skill in this field. This will now be provided.

The nystagmus eye movements consist of two components, namely: (i) a "slow phase", in which the eye drifts at an angular velocity close to that of the drifting visual stimulus, and (ii) shorter quick return eye motions which serve to rapidly reset the eye position for subsequent continued slow phase motion. The repetitive nature of the nystagmus eye motions leads to the interval between subsequent slow phase motions to be referred to as an OKN "beat". OKN beats can occur either contiguously or occasionally. There may be intervals of time, referred to here as "gaps", in which there are no OKN beats. Groups of contiguous beats separated by gaps of no nystagmus activity are referred to as being "clustered".

The terms "total variation" (TV) and "relative total variation" (RTV) are defined by the following relationships:

$$TV = \Sigma |v(i) - v(i+1)| \quad 0 < i < N-1$$

(where || denotes the absolute value, v(i) is the ith OKN slow phase velocity in the eye position record, and N is the total number of recognized OKN beats); and $$RTV = TV/SDOKS$$

(where SDOKS is the standard deviation in the OKN beat deflection in degrees).

TV is designed to give an indication of the smoothness of the variation in the OKN slow phase velocity over time. RTV is simply a scaled version of TV which attempts to address the possibility of different absolute beat sizes in different persons.

Some of the parameters in the above list are described as being based on OKN beats whose slow phase drift is well fit by straight lines, such as: SDwfOKT, MwfOKT and MwfOKS. All OKN beats data were plotted on a graph and were initially fit by eye using a graphical method. Each beat was subsequently fit by linear regression. "Well fit" OKN beats were those whose goodness of fit statistic (r) was greater than 0.85. The outcome of the initial discriminate analysis was that the OKN variables listed in Table 1 (below) could be used for a discriminant function to distinguish subjects in the normal group from subjects in the test group.

TABLE 1

Basic Discriminant Analysis (A) OKN Variables remaining in discriminant analysis:

| | |
|---|---|
| $SDV_1$ | $SDclOKT_4$ |
| $SDV_4$ | $MclOKR_1$ |
| $SDOKT_2$ | $MclOKS_2$ |
| $MwfOKT_3$ | $RTVwf_3$ |
| $SDwfOKT_2$ | $RTVwf_4$ |
| $CLwfOKT_2$ | |

(B) Classification Results:

| | | PREDICTED GROUP | |
|---|---|---|---|
| ACTUAL GROUP | CASES | test | normal |
| test | 7 | 7 | 0 |
| | | 100.0% | 0.0% |
| normal | 10 | 0 | 10 |
| | | 0.0% | 100.0% |

Percentage of cases correctly classified: 100.00%

The names of the variables (parameters) of Table 1 correspond to the definitions provided above and the subscripts refer to the experiment types or stimulus paradigms. Thus, $SDV_1$ refers to the standard deviation in the slow phase velocities obtained in experiments with 27.2 Hz temporal modulation of contrast, producing the frequency doubled illusion, and where the stimulus moved from left to right. The discriminant function was used with roughly equal numbers of (a) type 1 and type 2 experimental variables, arising from frequency doubled stimuli, and (b) type 3 and type 4 stimulus paradigms.

Since previous scientific experiments have revealed that visual performance measured in response to frequency doubled stimuli is highly correlated with glaucomatous damage (see the specifications of Australian patent No 611,585 and the corresponding U.S. Pat. No. 5,065,767), it was decided to examine the discriminating power of the best five experiment type 1 and type 2 variables. Table 2 shows the outcome of discriminant analysis using the best 5 of the experiment type 1 and type 2 variables (listed in the top part of Table 2). The total variation in the OKN beat velocities from type 1 experiments, $TV_1$, was highly correlated with the test group and so a second analysis was performed substituting $TV_1$ for $SDV_1$. However, this substitution did not alter the outcome of the discriminant analysis, which is summarized in the lower part of Table 2. Discrimination was good but produced a false positive rate of about 14 per cent.

TABLE 2

Best 5 Frequency Doubled Variables (A) Discriminant analysis using best 5 frequency doubled variables from Table 1

$CLwfOKT_2$
$SDV_1$ or $TV_1$
$SDOKT_2$
$MclOKS_2$
$MclOKR_1$ (B) Classification Results:

| | | PREDICTED GROUP | |
|---|---|---|---|
| ACTUAL GROUP | CASES | test | normal |
| test | 7 | 6 | 1 |
| | | 85.7% | 14.3% |
| normal | 10 | 1 | 9 |
| | | 10.0% | 90.0% |

Percentage of cases correctly classified: 88.24%

Another aspect of the OKN data was that many of the variables related to the OKN beat time were correlated with age. Therefore, it was thought reasonable to eliminate these variables and perform the discriminant analysis again on the basis of the remaining variables. The results of this exercise are shown in Table 3. The best 5 variables were again explored and it was found that these variables had very good discriminating power. In particular, these variables produced no false positives, only false negatives, with about 14.3 percent of the test group appearing to be classified as normal. This result was not unexpected, for it was reasonable that some of the glaucoma suspects did not, in fact, have any glaucomatous damage.

TABLE 3

No-OKT Variables (A) OKN Variables remaining in discriminant analysis:

| | |
|---|---|
| $SDV_2$ | $MclOKR_1$ |
| $SDV_4$ | $MclOKR_4$ |
| $MOKR_3$ | $TV_4$ |
| $MOKR_4$ | $RTVwf_1$ |
| $MedGapT_1$ | $RTVwf_3$ |
| $SDGapT_2$ | $RTVwf_4$ |
| $SDGapT_3$ | |

(B) Classification Results:

| | | PREDICTED GROUP | |
|---|---|---|---|
| ACTUAL GROUP | CASES | test | normal |
| test | 7 | 7 | 0 |
| | | 100.0% | 0.0% |
| normal | 10 | 0 | 10 |
| | | 0.0% | 100.0% |

Percentage of cases correctly classified: 100.00%

Thus it has been demonstrated that the present invention provides an effective technique for ascertaining whether a subject has suffered glaucomatous damage.

It will be appreciated that a specific exemplification of the present invention has been described above, and that variations in, and modifications of, the exemplification can be made without departing from the present inventive concept. For example, the regular or periodic pattern that is drifted laterally may be oriented with the striations or other distinct periodic features of the pattern extending in a direction which is not vertical, so that the drifting of the pattern is not strictly to the left or to the right, but is in a direction which is orthogonal to the direction in which the striations or other distinct periodic features extend.

I claim:

1. A method for diagnosing the occurrence of glaucoma in a subject, said method comprising the steps of:

(1) presenting to the subject a regular pattern, having distinct vertical features, and causing the pattern to move laterally to either the left or the right, at a constant rate; said distinct vertical features comprising a relatively low spatial frequency, or a collection of relatively low spatial frequencies, and having a contrast which is modulated at a relatively high temporal frequency, said modulation being effected by a translation of the pattern image across the subject's retina and/or by direct contrast modulation of the pattern features, at a frequency which is sufficient, or nearly sufficient, for a frequency doubled visual illusion to be perceived by a person of normal vision who observes said pattern;

(2) monitoring an optokinetic nystagmus of the subject during the movement of the pattern and determining at least one of the parameters in the group consisting of (a) standard deviation of optokinetic nystagmus slow phase velocity;

(b) standard deviation of an optokinetic beat duration;

(c) mean optokinetic nystagmus heat duration for optokinetic nystagmus beats having a slow phase which is well represented in a graphical display by a straight line;

(d) standard deviation of the optokinetic nystagmus beat duration for optokinetic nystagmus beats having a slow phase which is well represented in a graphical display by a straight line;

(e) 95 percent confidence limit in a mean duration of optokinetic nystagmus beats for beats which have a slow phase eye position with time which is well represented in a graphical display by a straight line;

(f) standard deviation of optokinetic nystagmus beats which occur within contiguous clusters of beats;

(g) mean rate of optokinetic nystagmus beats which occur within contiguous clusters of beats;

(h) mean eye deflection per optokinetic nystagmus beat of optokinetic nystagmus beats which occur within contiguous clusters of beats; and (i) relative total variation in optokinetic nystagmus beat velocity for optokinetic nystagmus beats which have a slow phase that is well represented by a straight line; and (3) comparing each of the determined parameters with a value of that parameter expected for a person with normal, healthy vision.

2. A method as defined in claim 1, in which at least the parameters (a), (b), (e), (g) and (h) are determined and are compared with the values of these parameters expected for a person with normal, healthy vision.

3. A method as defined in claim 1, in which said pattern is a sinusoidal grating pattern with substantially vertical striations.

4. A method as defined in claim 3, in which the lateral movement of said pattern is at a rate within the range of from 4 pattern cycles per second to 10 pattern cycles per second.

5. A method as defined in claim 1, in which the lateral movement of said pattern is at a rate within the range of from 4 pattern cycles per second to 10 pattern cycles per second.

6. A method as defined in claim 1, in which said pattern is described by the function $I(x,t)$ defined by the relationship $$I(x,t) = I_0 + C(t)I_0 \sin[2\pi(fx - \omega t)]$$

where $I_0$ is the background intensity, $C(t)$ is a function describing the temporal modulation of the contrast, $f$ is the spatial frequency with units of cycles per degree, $\omega$ is the temporal frequency generated by the drift of the pattern with units of Hz, and $x$ and $t$ correspond to space and time measured in degrees and seconds, respectively.

7. A method as defined in claim 6, in which: $C(t)$ is a square wave, modulated at the rate of 27.2 Hz; the spatial frequency is 0.25 cycles per degree of the subject's vision; and the lateral movement of said pattern is at the rate of 6.79 Hz.

8. A method for diagnosing the occurrence of glaucoma in a subject, said method comprising the steps of (1) presenting to said subject a grating pattern having sinusoidal striations or other distinct periodic features extending in a first direction and causing the pattern to move in a second direction at a constant rate, said second direction being orthogonal to said first direction; said striations or periodic features having a relatively low spatial frequency, or a collection of relatively low spatial frequencies, and having a contrast which is modulated at a relatively high temporal frequency, said modulation being effected by a translation of the pattern image across the subject's retina and/or by direct contrast modulation of the pattern features, at a frequency which is sufficient, or nearly sufficient, for a frequency doubled visual illusion to be perceived by a person of normal vision who observes said grating pattern;

(2) monitoring an optokinetic nystagmus of the subject during the movement of the pattern and determining at least one of the parameters in the group consisting of (a) standard deviation of optokinetic nystagmus slow phase velocity;

(b) standard deviation of an optokinetic beat duration;

(c) mean optokinetic nystagmus beat duration for optokinetic nystagmus beats having a slow phase which is well represented in a graphical display by a straight line;

(d) standard deviation of the optokinetic nystagmus beat duration for optokinetic nystagmus beats having a slow phase which is well represented in a graphical display by a straight line;

(e) 95 percent confidence limit in a mean duration of optokinetic nystagmus beats for beats which have a slow phase eye position with time which is well represented in a graphical display by a straight line;

(f) standard deviation of optokinetic nystagmus beats which occur within contiguous clusters of beats;

(g) mean rate of optokinetic nystagmus beats which occur within contiguous clusters of beats;

(h) mean eye deflection per optokinetic nystagmus beat of optokinetic nystagmus beats which occur within contiguous clusters of beats; and (i) relative total variation in optokinetic nystagmus beat velocity for those optokinetic nystagmus beats which have a slow phase that is well represented by a straight line; and (3) comparing each of the determined parameters with a value of that parameter expected for a person with normal, healthy vision.

9. A method as defined in claim 8, in which at least the parameters (a), (b), (e), (g) and (h) are determined and are compared with the values of these parameters expected for a person with normal, healthy vision.

10. A method as defined in claim 9, in which the lateral movement of said pattern is at a rate within the range of from 4 pattern cycles per second to 10 pattern cycles per second.

11. A method as defined in claim 8, in which said pattern is described by the function I(x,t) defined by the relationship $$I(x,t) = I_O + C(t)I_O \sin[2\pi(fx - \omega t)]$$

where $I_O$ is the background intensity, C(t) is a function describing the temporal modulation of the contrast, f is the spatial frequency with units of cycles per degree, $\omega$ is the temporal frequency generated by the drift of the pattern with units of Hz, and x and t correspond to space and time measured in degrees and seconds, respectively.

12. A method as defined in claim 11, in which C(t) is a square wave, modulated at the rate of 27.2 Hz; the spatial frequency is 0.25 cycles per degree of the subjects vision; and the lateral movement of said pattern is at the rate of 6.79 Hz.

13. A method as defined in claim 8, in which the lateral movement of said pattern is at a rate within the range of from 4 pattern cycles per second to 10 pattern cycles per second.

* * * * *